(12) United States Patent
Mayer

(10) Patent No.: US 11,173,320 B2
(45) Date of Patent: Nov. 16, 2021

(54) PROBE DEVICE, SYSTEM AND METHOD FOR PHOTOBIOMODULATION OF TISSUE LINING A BODY CAVITY

(71) Applicant: Esther Mayer, Ra'anana (IL)

(72) Inventor: Esther Mayer, Ra'anana (IL)

(*) Notice: Subject to any disclaimer, the term of this patent is extended or adjusted under 35 U.S.C. 154(b) by 593 days.

(21) Appl. No.: 14/981,450

(22) Filed: Dec. 28, 2015

(65) Prior Publication Data
US 2016/0129278 A1 May 12, 2016

Related U.S. Application Data

(63) Continuation of application No. 13/644,689, filed on Oct. 4, 2012, now abandoned, which is a continuation of application No. 11/910,330, filed as application No. PCT/IL2006/000410 on Mar. 30, 2006, now abandoned.

(60) Provisional application No. 60/666,618, filed on Mar. 31, 2005.

(51) Int. Cl.
*A61N 5/06* (2006.01)
*A61N 5/073* (2006.01)

(52) U.S. Cl.
CPC ......... *A61N 5/0603* (2013.01); *A61N 5/0624* (2013.01); *A61N 2005/063* (2013.01); *A61N 2005/0605* (2013.01); *A61N 2005/0606* (2013.01); *A61N 2005/0607* (2013.01); *A61N 2005/0608* (2013.01); *A61N 2005/0611* (2013.01); *A61N 2005/0644* (2013.01); *A61N 2005/0652* (2013.01); *A61N 2005/0659* (2013.01); *A61N 2005/0663* (2013.01); *A61N 2005/073* (2013.01)

(58) Field of Classification Search
CPC ................................ A61B 18/20; A61N 5/06
USPC ..................................... 606/2–19; 607/88–94
See application file for complete search history.

(56) References Cited

U.S. PATENT DOCUMENTS

| 1,771,076 | A | * | 7/1930 | Chesney | ............. | A61N 5/0603 607/92 |
| 3,224,432 | A | | 12/1965 | Billingsley | | |
| 4,800,478 | A | | 1/1989 | Takahashi | | |
| 4,804,240 | A | | 2/1989 | Mori | | |
| 5,041,109 | A | * | 8/1991 | Abela | ................. | A61B 5/0422 606/15 |

(Continued)

FOREIGN PATENT DOCUMENTS

| DE | 20115123 U1 | 12/2001 |
| EP | 763371 A2 | 3/1997 |

(Continued)

OTHER PUBLICATIONS

Ion Laser; Wikipedia.*
Argon Ion Lasers; RP Photonics Encyclopedia.*

*Primary Examiner* — Lynsey C Eiseman
(74) *Attorney, Agent, or Firm* — Browdy and Neimark, PLLC

(57) ABSTRACT

A device is presented for use in treatment of tissues inside a body cavity. The device comprises a probe member having at least a portion thereof carrying a plurality of light sources, at least said portion of the probe member having dimensions and shape suitable for insertion into a certain body cavity and for arranging within the surface thereof a three-dimensional array of said light sources, the light sources being configured and operable to irradiate optical energy outwardly from said probe member.

19 Claims, 7 Drawing Sheets

(56) References Cited

U.S. PATENT DOCUMENTS

| | | | |
|---|---|---|---|
| 5,066,291 A * | 11/1991 | Stewart | A61B 18/20 359/326 |
| 5,445,608 A * | 8/1995 | Chen | A61N 5/0601 604/19 |
| 5,454,782 A * | 10/1995 | Perkins | A61B 18/1477 604/20 |
| 5,616,140 A | 4/1997 | Prescott | |
| 5,683,436 A | 11/1997 | Mendes | |
| 5,766,234 A | 6/1998 | Chen et al. | |
| 5,800,478 A | 9/1998 | Franco | |
| 5,989,245 A | 11/1999 | Prescott | |
| 6,083,218 A | 7/2000 | Chou | |
| 6,416,531 B2 | 7/2002 | Chen | |
| 6,514,277 B1 * | 2/2003 | Lilge | A61N 5/0601 422/82.08 |
| 6,607,525 B2 | 8/2003 | Franco | |
| 6,692,490 B1 | 2/2004 | Edwards | |
| 6,764,501 B2 | 7/2004 | Ganz | |
| 6,887,260 B1 | 5/2005 | McDaniel | |
| 6,986,764 B2 | 1/2006 | Davenport et al. | |
| 7,198,633 B1 | 4/2007 | Starwynn | |
| 7,526,344 B2 | 4/2009 | Kim | |
| 7,975,699 B2 | 7/2011 | Hyde et al. | |
| 2003/0023283 A1 | 1/2003 | McDaniel | |
| 2003/0076281 A1 | 4/2003 | Morgan et al. | |
| 2003/0097122 A1 | 5/2003 | Ganz et al. | |
| 2004/0111133 A1 | 6/2004 | Huculak et al. | |
| 2004/0116985 A1 | 6/2004 | Black | |
| 2004/0193235 A1 | 9/2004 | Altshuler et al. | |
| 2004/0193236 A1 | 9/2004 | Altshuler et al. | |
| 2005/0004631 A1 * | 1/2005 | Benedict | A61N 5/0619 607/88 |
| 2005/0024853 A1 | 2/2005 | Thomas-Benedict | |
| 2005/0106710 A1 * | 5/2005 | Friedman | F21S 4/20 435/287.1 |
| 2005/0131497 A1 | 6/2005 | Suzuki | |
| 2006/0136021 A1 | 6/2006 | Sutton | |
| 2006/0183072 A1 | 8/2006 | Black | |
| 2007/0073362 A1 * | 3/2007 | Campbell | A61N 5/0603 607/88 |

FOREIGN PATENT DOCUMENTS

| | | |
|---|---|---|
| WO | 00/32121 A1 | 6/2000 |
| WO | 03/017824 A2 | 3/2003 |
| WO | 05/011606 A2 | 2/2005 |

* cited by examiner

PROBE DEVICE, SYSTEM AND METHOD FOR PHOTOBIOMODULATION OF TISSUE LINING A BODY CAVITY

FIELD OF THE INVENTION

This invention is in the field of photobiomodulation, and relates to an optical probe device, system and method for affecting tissue by light.

BACKGROUND OF THE INVENTION

Photobiomodulation covers a wide range of topics that are important to all living creatures. One such topic includes photomedicine, the studies of both the detrimental effects of light as well as the beneficial effects of light (e.g. phototherapy or light therapy).

For the past two decades, the medical properties of light have been investigated rigorously, both in the laboratory and in the clinic, to delineate its mechanisms and potential clinical applications. It has been established that light interferes with a number of cellular processes, including protein synthesis (e.g. collagen production), cell growth and differentiation, cell motility, membrane potential and binding affinities, neurotransmitter release, ATP synthesis, and others, similar to photosynthesis in plants. Further, different wavelengths have been shown to produce different healing effects at the biochemical, cellular, histological, and functional levels.

Whether using low intensity radiation in the visible, filtered ultraviolet or near infrared region from a laser, or a filtered incandescent lamp, phototherapy was shown to be beneficial in a number of clinical situations, from pain remission, to wound healing.

For example, external phototherapy has been shown effective in treating various acute and chronic medical conditions. For example, certain light spectra are effective in treating severe second degree burns, leg ulcers, bulimia nervosa, herpes, psoriasis, eczema, seasonal affective disorder, sleep disorders, acne, skin cancer, inflammatory and autoimmune conditions such as rheumatoid arthritis and deep tissue inflammation, muscular strains, varicouse veins, rosacea, and other conditions. One of the conditions most widely treated with phototherapy is hyperbilirubinemia in newborn infants, typified by an elevated level of a toxic molecule known as bilirubin in the infant's blood.

A blue light LED system which has received clearance from the U.S.A. Food and Drug Administration (FDA) is used for treating a range of skin conditions including moderate inflammatory acne vulgaris and various oral diseases such as stomatitis and gingivitis.

In addition, photobiomodulation is widely used for cosmetic applications, e.g. for skin rejuvenation and wrinkle smoothing.

European Patent No. 0 763 371 describes a method and apparatus for treating skin by applying pulsed light to the skin to heat and shrink collagen within the skin, thereby reviving the elasticity of the collagen and of the skin. The epidermis and outer layers of the skin may be protected by cooling with a transparent substance, such as ice or gel, to the skin. The temperature distribution within the skin is controlled by controlling the delay between the time the coolant is applied, and the time the light is applied, by controlling the pulse duration and applying multiple pulses, and by filtering the light and controlling the radiation spectrum. The spectrum includes the light having a wavelength in the range of 600-1200 nm. The pulsed light may be incoherent, such as that produced by a flashlamp, or coherent, such as that produced by a Nd(Yag) laser or a ruby laser, and may be directed to the skin using a flexible or rigid light guide.

In addition, Light Bioscience has developed methods where electromagnetic radiation, in particular, light, is used to photobiomodulate the activity of living cells to delay, diminish, retard or even reverse the structural and functional effects of aging of the living cells and tissues (e.g. skin cells, hair) as well as for the treatment of acne, as also described in WO 05/011606, WO 03/017824 and WO 00/032121.

WO 00/032121 describes a system for producing preferential damage to hair exiting mammalian skin. An agent having an average diameter for enabling the agent to penetrate the hair duct is selected. The agent is designed to attach to, or become physically incorporated into, the hair shaft, the hair follicle, the hair bulb or the hair duct. The agent has an electromagnetic radiation absorption characteristic which enables the agent to absorb a first wavelength of electromagnetic radiation from a skin-penetrating electromagnetic radiation source, such as a laser. The agent is applied to the skin so that the agent penetrates the skin and attaches to or becomes physically incorporated into the hair shaft, the hair follicle, the hair bulb or the hair duct. The agent is exposed to the first wavelength of electromagnetic radiation and absorbs the first wavelength of electromagnetic radiation.

According to the technique of WO 03/017824, skin disorders are treated by applying a photomodulation enhancing agent to the skin proximate to or directly to a target living tissue; and exposing the photomodulating enhancing agent to a source of electromagnetic radiation. The latter has at least one dominant emissive wavelength between about 300 nm and about 1400 nm. The source of electromagnetic radiation is selected from an ultrasound radiation emitter, a light emitting diode, a laser diode, a dye laser, metal halide lamps, a flashlamp, a mechanically filtered fluorescent light source, a mechanically filtered incandescent or filamentous light source, or combinations thereof. The photomodulation enhancing agent has an absorption characteristic at said dominant emissive wavelength selected to cause the inhibition of; reduction in size of, or the destruction of said target tissue.

The technique WO 05/011606 is aimed at improving the appearance, structure, function of aging skin, including up and down regulating the genotypic markers for the phenotype of aging skin. More than one light source of narrow-band, multichromatic electromagnetic radiation is used, wherein at least one light source emits radiation at a wavelength corresponding to yellow light and at least one light source emits radiation corresponding to infra-red light.

SUMMARY OF THE INVENTION

There is a need in the art to facilitate reconstitution of tissue lining walls of body cavities, having an orifice on the external surface of the body and an inner wall covered by biological vital cell, containing tissue, for example vagina, rectum, nostrils, oral cavity, etc. For example, when the body cavity is the vagina, there is a need to provide means for the rejuvenation of vaginal wall, which includes increasing flexibility, elasticity and firmness of the vaginal wall, resulting in the decrease in the internal vagina diameter. Moreover, there is a need in the art for a treatment device of a simple configuration to be operated by user and/or by the physician, allowing the device or at least that part thereof which is brought in adjacency with the body cavity to be disposable, as well as ensuring reliable device operation which is painless, non ablative and has no danger to the patient's body (e.g. no excessive heating of the tissue, no cancerogenic effect, sterile), as well as eye safe to the patient and physician.

The present invention is based on the understanding that collagen and elastin included in the sub-mucosal layer covering body cavities contribute to the elasticity and tone of these cavities. Their breakdown and disruption through, for example, the aging process, birth giving (when the body cavity is the vagina), the existence of a pathological condition. (e.g. inflammation or any other disease or disorder) etc. may result in loss of tightness and flexibility of the wall of the respective body cavity. Loss of tightness and flexibility may have impact on the wellbeing (physical as well as mental) of the subject suffering from the condition. Thus, there is interest in providing means for rejuvenation and reconstruction of the cavity's wall. With vaginal relaxation, the muscles are relaxed and have poor tone, strength, and control. The internal and external diameters increase. Under these circumstances, the vagina is no longer at its optimum functional state. As a result, the sensual side of sexual fulfilment is diminished.

In general, the present invention concerns a device, a system and a method for photobiomodulation, utilizing illumination of the walls of a body cavity with low-intensity light of one or more specific wavelengths within the visible spectral range. The term "photobiomodulation" relates to the use of light to induce an effect on a biological tissue or cell as well as deep into the tissue at the illuminated area. The effect may be the induction, stimulation or inhibition of a biochemical process so as to optimize inter alia, one or more of blood circulation within the tissue, oxygen supply, regulation of tissue functions, cell metabolism, cell respiration, cell renewal, tissue development and stability, tissue elasticity, tissue protection, tissue suppleness, and moisturizing of the tissue. The illumination results, inter alia, in a therapeutic beneficial effect, as detailed below.

According to the invention, a plurality of light emitters is used being arranged in an array along a housing (probe). The illumination may or may not be monochromatic, i.e. it may include mono or polychromatic light. The term monochromatic denotes a single wavelength (single color) while the term polychromatic denotes two or more wavelengths (two or more colors, e.g. red and blue). The illumination may be applied in continuous wave (CW) mode, or may be applied in a pulse mode at either fixed or variable frequency.

Generally, suitable light sources may include but are not limited to LEDs and lasers. Preferably, the invention utilizes LEDs, especially because they are low-intensity light sources which on the one hand cannot apply extra heating to the tissues under treatment which is essential when dealing with treatment inside a body cavity, such as vagina treatment, and on the other hand do not need to be cooled. Comparing the use of LED illumination for treatment of tissues with that of laser illumination, the following should be noted. Led illumination, while it might need a greater treatment time, provides for concurrently illuminating the entire region of interest rather than a point-like location; provides a more safe treatment; does not apply thermal energy to the tissue; and provides for affecting multiple types of tissues. The use of LEDs for treatment is relatively "non invasive", using a non coherent light.

The use of an array of spaced-apart LEDs when arranged close to the tissue region to be treated provides for substantially uniform illumination of the entire treatment region, eliminating a need for light collecting optics. For example, LEDs of primary colors, RGB, may be used to treat specific medical conditions by affecting biochemical processes within a biological cell or a tissue.

It should also be noted that, generally, a single high-intensity, and preferably broadband, light source (e.g. LED) can be used for illuminating a region in the vicinity thereof. This can utilize a high divergence of light emitted from the LED, or reflector/diffuser can be used at the LED output to direct the emitted light to the large target area. Also, when using more than one LED, a reflector/diffuser can be appropriately provided.

It should be noted that the invention may utilize a suitable polarizer unit for increasing the part of the emitted light effectively applied to tissue.

In some embodiments of the invention, single wavelength light (generally, narrow wavelength range) is applied to a biological tissue covering the inner wall of a body cavity, as the desired cellular response is heightened when a narrow wavelength band is applied. In some other embodiments of the invention a plurality of wavelengths are applied to the tissue. Since the problem to be solved by the vaginal treatment for example is a result of multi factorial variables (relaxation, dryness etc.), the treatment should preferably be a combination of photomodulation sequential treatments in order to achieve maximal benefit.

For example, when treating vaginal relaxation there is a need to, on the one hand, enhance collagen and elastin production, and on the other hand increase blood circulation. Therefore, a single wavelength or a combination of multiple wavelengths applied in a sequence can be used. The technique disclosed herein may utilize white-color LEDs operable to emit short pulses of light of predetermined duration and period.

For example, a therapeutic effect can result from applying light with a narrowband of wavelengths centered about a dominant wavelength. The energy level for this process may for example be from about 200 mW/cm$^2$ to less than about 1000 mW/cm$^2$, in this specific but not limiting example, the exposure of the tissue to light is carried out by pulsing light with a period of pulses of less than 1 s, and the pulse duration from about 150 ms to about 850 ms.

Thus, in accordance with a first aspect of the present invention there is provided a device for use in treatment of tissues lining a body cavity, the device comprising a probe member having at least a portion thereof carrying a plurality of light sources, at least said portion of the probe member having dimensions and shape suitable for insertion into a certain body cavity and for arranging within the surface thereof a three-dimensional array of said light sources the light sources being configured and operable to irradiate optical energy outwardly from said probe member.

The term "probe member" or "probe" as used herein actually refers to an illuminating unit and is thus used interchangeably with the term "illuminator". The probe portion carrying the light sources may be appropriately curved, may have a symmetrical cylindrical shape, an egg-plant shape, as well as other shapes suitable for insertion into a body cavity; or may have a substantially rectangular cross section (e.g. with round edges or not) carrying the light sources at least within two opposites surfaces of the probe portion by which it faces the opposite inner walls of the body cavity when the device is in operation.

The "light source" carried by the probe member may be constituted by a light emitting element itself or by an optical window coupled (e.g. by fiber) to a light emitting element located outside the probe member or outside the portion of the probe member carrying the light source. The light emitting element is preferably a light emitting diode (LED), or can be a chemical light source, i.e., a chemiluminescent substance, for transmitting cool light energy into the body tissue.

In one embodiment of the invention, primary colors, red, green or blue or any combination of them, is employed. Blue and red light can generally be provided by an incandescent lamp or other suitable lamp, a LED, a combination of LEDs, a laser or chemical light source with preferred wavelengths predominantly between about 300 nm to about 1200 nm, and more preferably between about 300 nm to about 800 nm. It should be noted that different monochromatic light components may have different effects on a biological tissue. For example, red light affects blood circulation within the exposed tissue site (Ref 16). Thus, exposure of the inner wall of a body cavity to red light may increase blood circulation at the treated site. Further, blue light has an effect on bacteria and thus may be used to treat pathogen infections. Yet, yellow light has an effect on tissue rejuvenation.

Thus, in accordance with the invention, mono- as well as polychromatic light may be used to achieve one or more desired effects.

The term "body cavity" as used herein denotes any body cavity having an orifice on the external surface of the body and an inner wall covered by biological vital cell containing tissue. In a typical mammalian body such as the human body, the body orifices include the nostrils, the lacrimal ducts, the ears the mouth, the anus, nipples and breast ducts, secreting glands, the urethra, the uterine cervix canal, and the vagina.

The invention is particularly useful for affecting the tissue lining the inner walls of the vagina, the anus, the nostrils and the lacrimal ducts as well as deeper within the tissue. The invention is mainly intended for treatment of the inwall of the body cavity of the kind comprising a mucous membrane and submucous layer.

As appreciated, all body surfaces and cavities are covered by epithelial cells and there are numerous types of epithelial cells within the body: Simple squamous epithelium; Simple cuboidal epithelium; Simple columnar epithelium; Pseudostratified columnar epithelium; Stratified squamous epithelium (The keratinized (cornified) type and the nonkeratinized (noncornified) type); Stratifed cuboidal epithelium; and Transitional epithelium. While the skin mainly comprises keratinized starified squamous epithelium, it is noted that body cavities, which are the subject of the present invention, typically comprise nonkeratinized (noncornified) type epithelial cells (also called mucous membrane). Thus, in the context of the present invention, the wall of body cavities are those which mainly and essentially comprise mucous membrane and submucous layer.

The term "mucous membrane" refers to the lining of ectodermic origin, covered in epithelium (nonkeratinized (noncornified) type epithelial cells) and is involved in absorption and secretion. The mucous membrane lines various body cavities that are exposed to the external environment and internal organs. In the context of the present invention, the mucous membrane includes the nasal mucosa, the oral mucosa including the buccal and labial mucosa, the mucosa of the ear, the mucosa of the eye (e.g. lining the walls of the lacrimal duct), the rectal mucosa, the anal mucosa, and the genital mucosa, preferably, the mucosa at the vagina.

The invention also provides a system for photobiomodulation of a body cavity. The system comprises the above-described probe and a control unit. The control unit comprises an illumination controller configured and operable for adjusting at least one of the following operational parameters: an operational mode of the light emitter (located on the probe member or outside thereof and optically coupled thereto) to provide either one of the pulse and continuous-wave mode of operation for each wavelength used, a duration of the light pulse, a period of pulses, an intensity of the emitted light, wavelengths of the emitted light, and a duration of the illumination.

The illumination controller is a hardware and/or software preprogrammed for controlling one or more of the above parameters.

The device of the present invention is preferably configured as a hand-held unit including said probe member carrying the three-dimensional array of light sources, and a handle portion. The control unit may be entirely incorporated within the hand-held device, or may be an external unit connectable to the device, or the utilities of the control unit may be distributed between the probe device and the external unit (thus generally, the control unit may be at least partially incorporated within the hand-held device).

In yet a further aspect of the invention there is provided a method for treating a body cavity, by exposing at least a part of said body cavity wall to optical energy. According to a preferred embodiment of the invention, it is intended for treatment of said the body cavity wall of the kind comprising mucous membrane and a submucous layer; and the effect of illumination comprises a photobiomodulation of said mucous membrane cells and/or a submucous layer.

Thus, in accordance with the invention there is also provided a method for increasing mucous secretion within a body cavity having an inner wall, the method comprising illuminating at least a part of said body cavity wall with an optical energy while controlling at least one of the following parameters of illumination: either one of the pulse and continuous-wave mode of operation fir each wavelength used, a duration of the light pulse, a period of pulses, an intensity of the emitted light, wavelengths and/or polarization of the emitted light, and a duration of the illumination.

In accordance with one embodiment, the method comprises:

providing a hand-held device comprising a probe member carrying a plurality of light sources, the probe member having dimensions and shape suitable for insertion at least a portion of the probe member into the certain body cavity and for arranging a three-dimensional array of said light sources within said at least portion of the probe member, the light sources being configured and operable to irradiate optical energy outwardly from said probe member;

inserting said at least part of the probe member into a body cavity via an orifice of the body cavity such that a part of the probe member is located close to said orifice of said body cavity and is accessible to a user; and actuating said hand-held, device to illuminate at least a part of the inwall of said body cavity by said optical energy.

During the device operation, at least one of the following parameters is controlled: an operational mode of the light source to provide either one of pulse and continuous-wave mode of operation, a duration of the light pulse, a period of pulses, an intensity of the emitted light, wavelengths and/or polarization of the emitted light, and a duration of the illumination.

Illumination of cells and tissues may affect numerous biochemical changes in cellular membrane and intracellular and intercellular content. A monochromatic or polychromatic light, pulsed or continuous light may stimulate cytochromes in the body's tissue, which increase the energy metabolism of the cells, maximizing cell activity of damaged, aged or distressed tissue. The activity may occur both within the cell through a rapid increase of protein and calcium production, and between the cells by the improvement of cellular membrane channels and gap junctions via the increased production of protein resulting in enhanced blood circulation, fibroblastic activity and collagen and elastin production.

Further, in the mitochondria, enhanced ATP (adenosine triphosphate)—ADP (adenosine diphosphate) metabolism, may increase ATP content or a growth of the electric potential across inner membranes which in turn may lead to cellular activation and RNA and DNA synthesis, as appropriate. Moreover, growth factor response within the cells and tissues may be increased as a result of enhanced ATP and protein synthesis.

Thus, some beneficial effects of radiation may include, without being limited thereto and in addition to those already described hereinabove, accelerated regeneration of damaged tissue and improvement of blood circulation (e.g. due to vasodilation); beneficial development of new blood vessels; enhancement of cellular activity, such as of fibroblasts and phagocytes (which may be effective against infection or inflammation); enhancement of cell division and cell growth (such as of fibroblasts and phagocytes); stimulation and increasing support for the multi-production of protein production such as collagen and elastin fibers; enhancement of important specific enzymes involved in cell regeneration; pain relief as a result of endorphin release; immunostimulation due to, for example, increase in lymphocyte activity; or to provide an anti-inflammatory and/or anti edematous effect, increase of serotonin synthesis and secretion improving seasonal depression and postpartum blues.

In addition, radiation of the inner wall of a body cavity according to the invention may stimulate mucosal fluid or moist secretions of otherwise abnormally dried cavities or when such stimulation is desired.

It is well appreciated that the method may be applicable for the treatment of a variety of conditions which require for said treatment build up and reconstitution of an inwall of a body cavity as well as for the treatment of pathological conditions.

The term "treatment" in accordance with the invention is used to denote an effect of radiation on the structure and/or function of a body cavity as a result of a single or sequence of illumination sessions of the body cavity. Treatment may have a healing as well as a prophylactic effect on a damaged or distressed tissue forming the cavity's inwall leading to the elimination, inhibition or arrest in progression of any damage caused to said inwall, as well as relief in symptoms associated with damaged cavity inwall. Affected cavity wall may be a result of aging of the tissue lining the wall (exhibited by, inter alia, reduced tissue vitality, elasticity and tissue tone dryness and irritability) or as a result of a pathological condition associated with the tissue lining the wall (inflammation, trauma etc.).

As already noted above, treatment by optical energy increases cell activity of damaged or distressed tissue. The activity occurs both within the cell through a rapid increase of protein and calcium production and between the cells by the improvement of the cellular membrane channels and gap junctions via the increased production of protein, resulting in enhanced blood circulation, fibroblastic activity and collagen and elastin production. However, it is worth noting that light does not exert its beneficial action only on the site being exposed to light, but also through gentle stimulatory action on blood coursing through the fine capillaries under the tissue lining the body cavity being treated thereby increasing the supply of vital oxygen and energy to every cell.

According to one preferred embodiment, treatment (illumination of a body cavity) results in the reconstitution of the wall of the cavity. The term "reconstitution of a cavity wall" as used herein denotes not only the densification of the connective tissue constituting the wall (e.g. by stimulation the production of collagen and elastin) leading to the tightening of the wall, but also, and at times preferably, to the healing of mucous membrane lining the wall, so as to management of mucous secretion of an otherwise dry, tender and sore cavity.

Treatment in accordance with the invention may also include, in addition or alternatively, a healing or preventative effect on a pathological condition.

The term "pathological condition" denotes any ailment associated the tissue lining a body cavity, the treatment of which is not considered mere cosmetic treatment. This includes, inter alia, a condition selected from degenerative conditions caused by the aging process, inflammation, infection, vascular disorders, and many others, as known in the art. For example, the effect of radiation on a pathological condition (observed by accelerated regeneration of damaged tissue in the cavity and improvement of blood circulation in the cavity) may be associated with increased activity of certain cells like fibroblasts and phagocytes; enhanced cell division and cell growth; activation of the synthesis of proteins; improved blood circulation due to relaxation of vessel walls (vasodilation); reduced pain, swelling, inflammation and irritation; stimulated endorphins and serotonin and stimulation of healing processes; as well as reduction of mutated cells.

Treatment in accordance with the invention may include, in addition to the illumination of the wall of the cavity, topical application of a substance, such as a suitable photo-sensitizer. One example of a photo-sensitizer is 5-Aminolevulinic acid (ALA). The photo-sensitizer will typically be applied to the wall of the cavity before illumination (e.g. manually or by the aid of a suitable syringe). As appreciated, treatment may also be in combination with topical application of a therapeutic active agent, such as a drug or a pro-drug (e.g. a chemical compound which transforms into its active form once applied to the tissue, or as a result of illumination) or an immunostimulator, as known in the art.

It is noted that the topically applied active agents may have a local as well as systemic effect. Exposure of the inner wall of a cavity to light may thus result in an increased absorbance of the active agent by the tissue and thus increased blood levels of the agent. This is of particular interest in the case of intranasal administration of vaccines and fertility agents and various drugs.

It is noted that in accordance with the invention an effect may be achieved, without using thermal injury as a trigger for achieving the desired effect.

According to one embodiment, treatment comprises illumination the wall of a body cavity with a monochromatic light.

According to another embodiment, treatment may include illumination of the wall of the body cavity with a combination of monochromatic lights. The cavity may be exposed to the combination of lights at the same time, e.g. by using a probe having different types of light sources mounted thereon; or at different treatment sessions, e.g. by using probes with different light sources, such as a first probe providing red light and thereafter, in a following treatment session, providing a probe illuminating blue light.

Treatment may include a single treatment session, i.e. a single illumination session which may vary in duration (from seconds to minutes) or plurality (two or more) illumination sessions (e.g. illumination in pulses). When applying a plurality of illumination sessions, different lights may be applied in a single treatment session. Thus, for example, a single treatment session may include a combination of illumination sessions of different wavelengths, at a predetermined sequence. In addition, treatment may comprise a combination of a continuous illumination of a selected wavelength concomitant with pulsed illumination of a different wavelength.

Treatment may be a daily treatment, may include one or more illumination/treatment sessions per day, and may extend to more than one day of treatment, at times for a period of several months.

According to one embodiment, a treatment session may last for example 10 minutes during which the body cavity is subjected to a continuous or pulsed optical energy. It is noted that during a treatment session, a body cavity may be illuminated by a combination of wavelengths, some being continuous and some, pulsated.

Treatment efficacy will be determined by one or more suitable parameters known in the art and may include, for example, physical examination of the treated subject as well as the general feedback received from the subject (e.g. by using a suitable questionnaire provided to the subject).

As appreciated by those versed in the art of gynecology, aging as well as birth giving may lead to loosening of the vaginal wall, vaginal enlargement and vaginal dryness. This typically results in a woman's sexual dysfunction and dissatisfaction during intercourse, as well as other discomforts such as the presence of had odors and male partner dissatisfaction.

Female sexual dysfunction is a complex process, coordinated by the neurologic, vascular and endocrine systems. Individually, sexuality incorporates family, societal and religious beliefs, and is altered with aging, health status and personal experience. In addition, sexual activity incorporates interpersonal relationships, each partner bringing unique attitudes, needs and responses into the coupling. A breakdown in any of these areas may lead to sexual dysfunction. Sexual dysfunction can be subdivided into desire, erozal, orgasmic and sexual pain disorders. Sexual dysfunction may result from unsatisfying encounter or inadequate stimulation which may lead to a decrease in one or more of the following decreased orgasm, decreased desire, decreased arousal, painful sex, etc.

Thus, according to one embodiment, the method comprises illuminating at least a portion of the vaginal wall with optical energy for the reconstitution (rejuvenation) of the wall of the vagina. Rejuvenation includes, inter alia, increase in elasticity and firmness of the body wall, enhanced tone, strength, and control. It will effectively decrease the internal and outer (introitus) vaginal diameters, as well as build up the perineal body (the area immediately outside the vaginal and above the anus. Treatment also provides an aesthetic enhancement of the external vaginal structures, resulting in a more youthful look. Treatment also has an important impact on a woman's sexual satisfaction.

In accordance with another preferred embodiment, treatment may include, in addition or alternatively, alleviating ailments within the vagina, such as inflammation, and infections known as bacterial vaginosis.

Any one or a combination of the following effects may be observed following exposure of vaginal wall with optical energy, as disclosed herein: tightening of the vaginal canal; enhancing collagen and elastin production; improving blood circulation within the vaginal wall; moistening of the vaginal canal leading to reduced soreness and thus to enhanced sexual sensitivity; reducing vaginal irritation.

In accordance with another embodiment, the invention provides treatment by exposure to light of internal and external hemorrhoids. Hemorrhoids are painful, swollen veins in the lower portion of the rectum or anus. Internal hemorrhoids occur just inside the anus, at the beginning of the rectum, while external hemorrhoids occur at the anal opening and may hang outside the anus. Hemorrhoids, internal as well as external, are often inflamed. Thus, by exposing hemorrhoids to optical energy, one or more of the following may occur: increased blood circulation; improved in lymphatic drainage; improved phagocyte activity; increased collagen and elastin production; etc, thereby leading to treatment of hemorrhoids.

In accordance with yet another embodiment, the method provides photobiomodulation of tissue lining the intranasal wall, including, aged intranasal cavity, moisten dry nasal membranes which may cause discomfort, soreness, congested breathing, and even bleeding and the associated possibility of nasal infections. In addition, exposure of the intranasal wall to optical energy may lead to increase in blood circulation and vasodialation at the wall, which may increase intra-nasal absorption of medicaments. As indicated above, this may be of particular interest for the intranasal delivery of vaccines and fertility agents and drugs.

In accordance with yet another embodiment, the invention provides is photobiomodulation of tissue lining the inwall of lacrimal duct. This may be of significance for treating lacrimal duct infection (dacrocyocystitis), congenital lacrimal duct obstruction (tear duct obstruction) and the like, which may lead to infection and inflammation.

Further, in accordance with a preferred embodiment, the invention concerns photobiomodulation of tissue lining the gums in the oral cavity. One particular desired effect is for preventing or treating Gingivitis. Gingivitis is a form of periodontal disease wherein inflammation and infection destroy the tissues that support the teeth, including the gingiva (gums), the periodontal ligaments, and the tooth sockets (alveolar bone). Illumination of the inflamed gums, in accordance with the invention may result in reduced inflammation and faster healing of the gums.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF SOME EMBODIMENTS

The following are examples of some different concepts which are intended to describe some of the general design possibilities of the probe, but are in no way intended to limit the scope thereof. It is important to mention that the final shape of the probe can differ from the examples given herein. It is deemed that such designs can be modified in accordance with the specific application and specific body cavity to be treated.

Figure 1A:
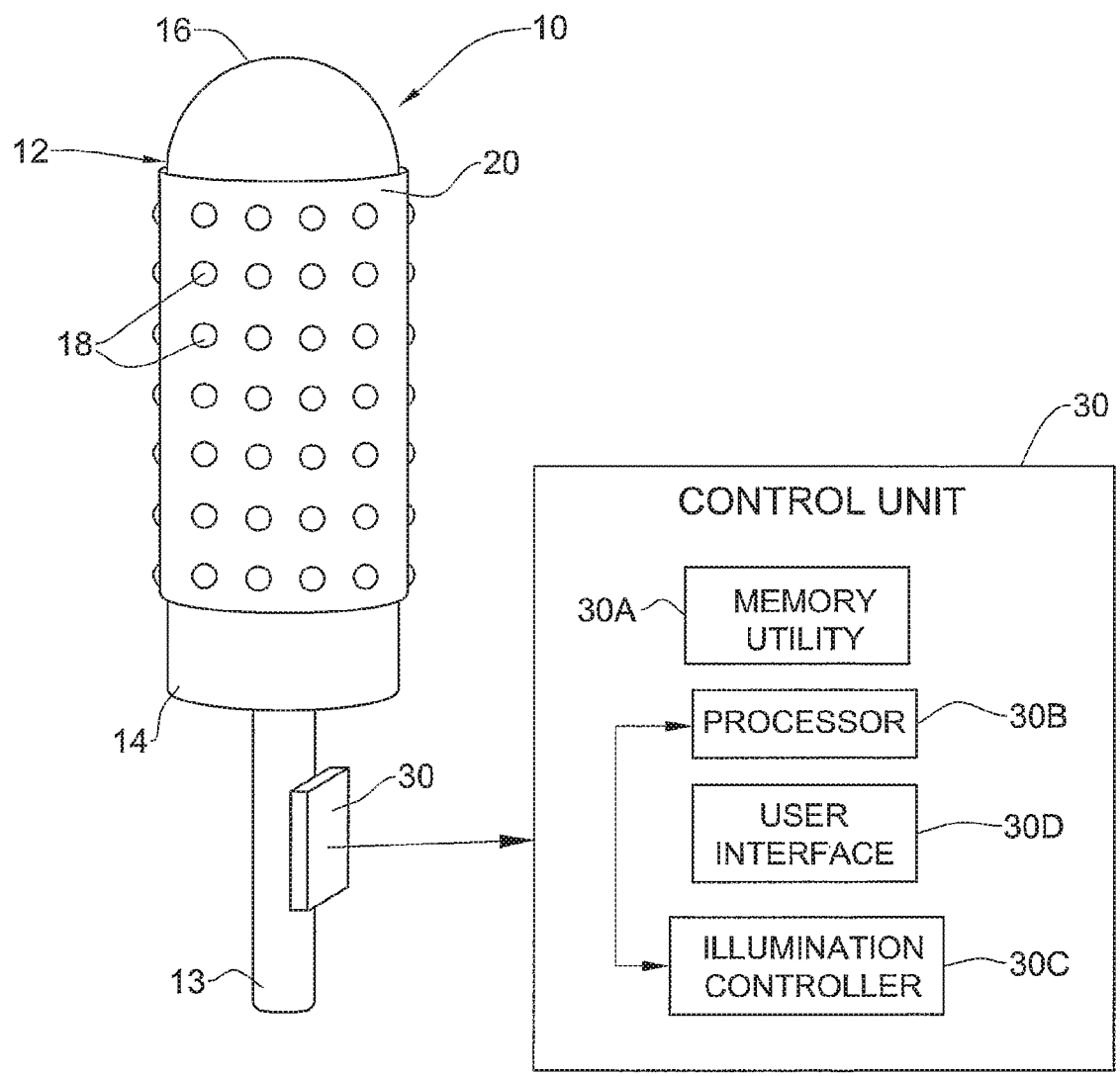
FIGS. 1A-1B schematically illustrate an example of a band-held probe device configured and operable according to the invention for treating the wall of a body cavity.
Figure 1B:
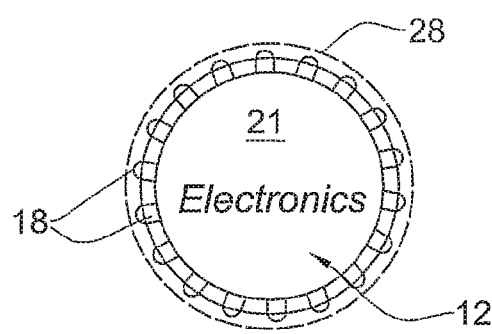

Reference is now made to FIGS. 1A and 1B illustrating schematically a probe device 10 for use in photobiomodulation of a body cavity in accordance with the invention. Device 10 comprises a probe member 12 having a distal end 14 to be located at the body cavity orifice when the device is put in operation and a proximal end 16 by which it is to be inserted into a body cavity. Probe member 12 carries a plurality of spaced apart light sources, generally at 18, arranged along of the surface of the probe member 12. Probe member 12 is configured (has dimensions and shape) allowing insertion of at least a part thereof into a certain body cavity and is configured to arrange on the surface of said at least portion of the probe member a three-dimensional array of the light sources. The latter are configured and operable to irradiate optical energy outwardly from probe member 12.

In the present non-limiting example, the probe member has a tampon-like configuration, i.e., has a cylinder- or tubular-like shape. As shown in FIG. 1A, proximal end 16 of such tampon-like member 12 has generally a hemispherical surface with no outwardly facing sharp points or edges so as to avoid inconvenient scraping of the walls of the body orifice and cavity, when inserting the probe via the cavity's orifice.

While in the specific embodiment illustrated in FIGS. 1A-1B cylindrical- or tubular-like probe member 12 has a circular cross-section, it is to be understood that the invention is not limited to this specific example, and the probe member may similarly function with an oval cross section, as well as be of a conical or eggplant-like shape, as well as not necessarily having a closed-loop configuration of its cross-section, etc.

As illustrated, probe device 10 has array of light sources 18. The term "array of light sources" denotes at least two, preferably more, light sources. Light sources may be constituted by light emitting elements themselves and (possible optics, such as lenses and/or polarizers and/or light diffusers, e.g. the lens may be implemented in a translucent diffusing material) arranged on the probe member/carrier in spaced-apart locations, or by optical windows (e.g. including optics, e.g. lenses and/or polarizers and/or light diffusers, e.g. the lens may be implemented in a translucent diffusing material) arranged in the spaced-apart locations on the probe member/carrier and optically coupled to external light emitting element(s) by light guides (fibers). This will be described further below with reference to FIGS. 3A-3B. The light sources may be randomly distributed or have a specific distribution pattern, e.g. in radially, longitudinally and/or diagonally arranged lines.

The probe member 12 or at least a apart thereof carrying the light, sources and intended to be inserted into the body cavity may be made of a rigid or flexible material. Preferably, the probe member is made of a relatively flexible material so as to reduce the chances of inadvertent injury to the body cavity. The probe member (or the outer cover as the case may be) is made of biocompatible material such as polycarbonate, polypropylene, acryl, and derivatives thereof, polyurethane, etc. as known in the art.

As shown in the example of FIGS. 1A-1B, array of LEDs 18 (constituting light sources) is associated with a suitable electronics, e.g. the LEDs are arranged within a printed circuit board (PCB) film 20. The latter wraps at least a part of the outer surface of the probe member 12. For example, such a PCB with LEDs may be configured as a cover mountable onto at least a part of the probe member. An electronic block 21 of the PCB arrangement is located inside the probe member 12 as shown in FIG. 1B. The device may be battery- or wall-powered, and permits convenient treatment of the patient as an office procedure. Many wavelengths can be used, depending on the type of treatment administered.

Figure 2:
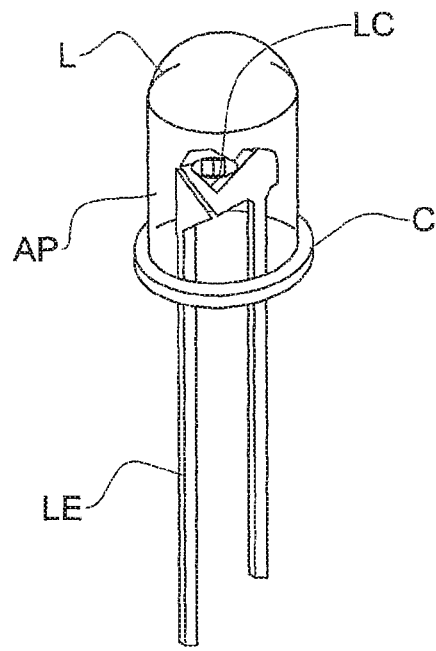
FIG. 2 schematically illustrates a typical LED configuration suitable to be used in the device of the present invention.

It is to be understood that any suitable LED configuration known in the art may be used in the present invention. FIG. 2 schematically illustrates an example of LED 18 suitable to be used in the device of the present invention. LED 18 includes a tubular Anode post AP, a Cathode C, a LED chip LC (formed by a silver die and attached gold wire bond on a top contact) inside the anode tube, an epoxy dome lens L, and a lead frame LF.

As exemplified in FIG. 1B by dashed curve, member 12 with LEDs 18 may be further coated by an external cover 22 made of a suitable biocompatible material, which is transparent for the spectral range(s) used, e.g. made of transparent latex. The cover material may be diffusive to direct light output from the light source to larger surface area. Preferably, such cover 22 is configured to be removably mountable onto member 12, thus enabling the cover to be disposable.

It should be noted that actually the entire probe carrying the LEDs may be disposable. Alternatively, the probe member may be configured as a two-part unit, where the two parts are appropriately engageable/disengageable, and that part (distal) of the probe which carries the LEDs (or optical windows as will be described further below) and is intended to be engaged with the body cavity (e.g. vagina) is disposable.

Turning back to FIG. 1A, probe 10 is appropriately formed with a handle portion 13 located at the distal end 14 of probe member 12. Also shown in FIG. 1A is a control unit 30 connectable to probe device 10, preferably by wires, or wireless. The control unit 30 is typically a computer system having inter alia such utilities as memory 30A, data processor 30B for operating the illumination via an illumination controller utility 30C, and a user interface 30D (including display). Control unit 30 also includes a battery power source (not shown) and/or a connector to a power network.

The control unit includes suitable hardware and software, and may be stored with certain reference data defining the operational mode of the LEDs per the user's treatment program. The latter includes for example the intensity of light, appropriate wavelength(s), pulsed or continuous wave (CW) operation, pulse rate and duration, duration of entire treatment session, as well as the personal data, etc.

For example, the applied light may be of intensity substantially not exceeding 1 Watt/cm$^2$; and may be pulsed with a period of about 1 ms, the illumination (treatment) duration may for example be in a range from 10 seconds to 1 hour.

For example, LEDs array 18 may include LEDs with a narrowband of wavelength centered about a dominant wavelength. The energy level may for example be from about 200 mW/cm$^2$ to less than 1000 mW/cm$^2$; the exposure of the tissue with light may be carried out by pulsing light with a period of pulses of about 1 ms, and the pulse duration from about 150 ms to about 850 ms.

It should also be noted, although not specifically shown, that probe device 10 could be equipped with a sensor unit including one or more sensors for sensing one or more conditions during the treatment. This may include temperature, level of secretion, chemical and biological sensors, etc.

Figure 3A:
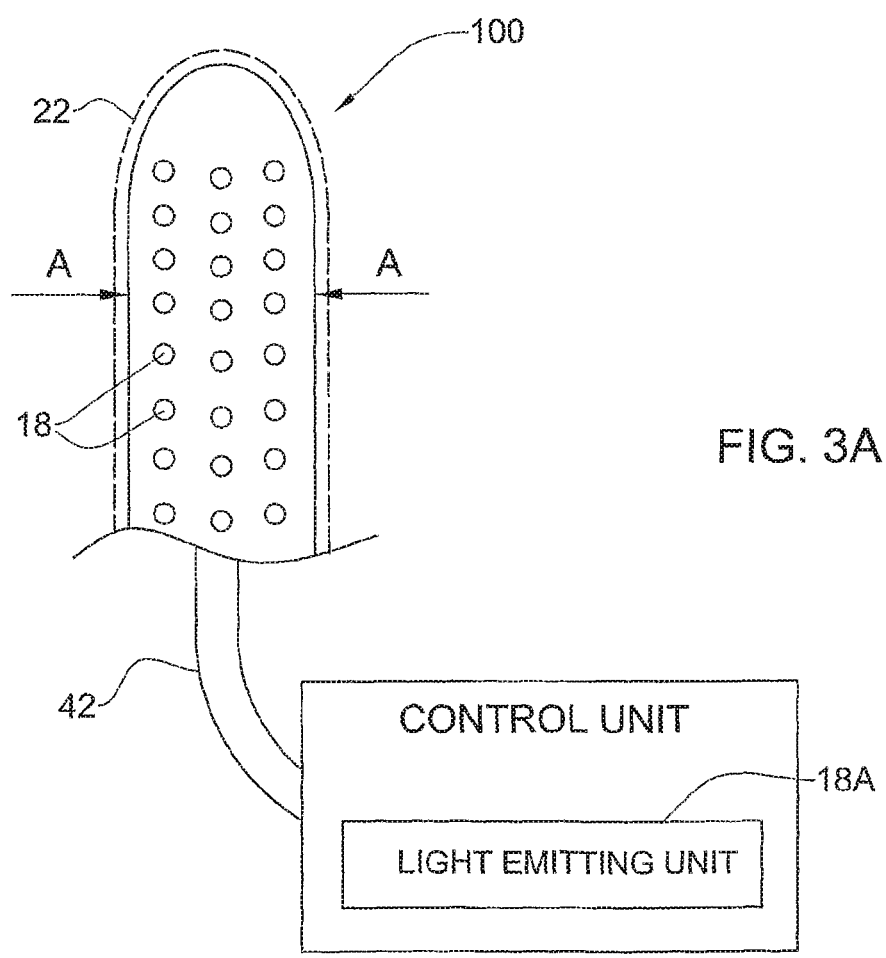
FIGS. 3A and 3B illustrate schematically another example of the probe device of the present invention, where an array of optical windows, formed in the probe member and optically coupled to external light emitter(s), constitute an array of light sources.
Figure 3B:
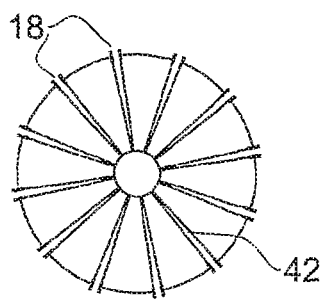

Reference is made to FIGS. 3A and 3B illustrating schematically another example of the probe configuration 100. To facilitate understanding, the same reference numerals are used for identifying components that are common in all the examples. FIG. 3A shows a partial side view of the probe, and FIG. 3B shows the cross-sectional view along line A-A in FIG. 3A.

Probe device 100 includes a cylindrical- or tubular-like or tampon-like probe member (housing) 12 formed along its circumference with an array of optical windows (e.g. apertures, or regions of a material translucent for the spectral range(s) used, and/or lenses) constituting light sources 18. An arrangement of fibers (light guides), generally at 42, is provided for optically coupling the optical windows to a light emitting unit 18A located outside the probe member 12 or outside that part of the probe member which is to be inserted into the body cavity. In the present not limiting example, the light emitting unit is accommodated in a control unit 30. As shown in FIG. 3B, each optical window is coupled to its dedicated segment of the fiber.

It should be understood although not specifically shown that the same fiber, that guides light of a specific color from an external light emitter, may be associated with a plurality of optical windows. This can be implemented by forming optical windows (e.g. perforations or translucent regions) in appropriate locations along the fiber.

The light emitting unit may include a single light emitter (of a narrow or broad band of emitted light), or an array of light emitters generating light of different colors. Also, different colors can be appropriately mixed and guided to the respective optical window(s) on the probe member 12. It should also be understood that with the configuration of FIGS. 3A-3B, a transparent cover 22 may be used (as shown in FIG. 3B) or may not, since the entire probe member 12 or respective part thereof with optical windows 18 can be disposable.

Figure 3C:
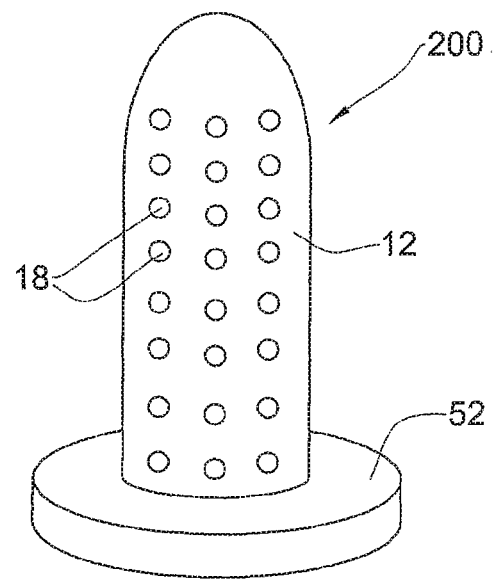
FIG. 3C schematically illustrates yet another example of a probe device of the present invention, equipped with an orifice abutment skirt at the DISTAL end of the probe member.

Reference is made to FIG. 3C schematically showing yet another example of a probe 200. Probe 200 is configured generally similar to either one of the herein described examples, namely including a tampon-like probe member 12 carrying a three dimensional array of light sources 18, and is further equipped with an orifice abutment skirt 52 at the distal end 14 of probe member 12. The skirt has a cross-sectional area greater than that of probe member 12 and extends radially outward from the periphery of probe member 12 thereby limiting the insertion of probe member 12 into a body cavity. The skirt (or a part thereof) may be made of a suitable (e.g. biocompatible) rigid or semi-rigid material so as to enable support of the probe against the lips of the cavity's orifice, while radiating the interior of the cavity.

Figure 3D:
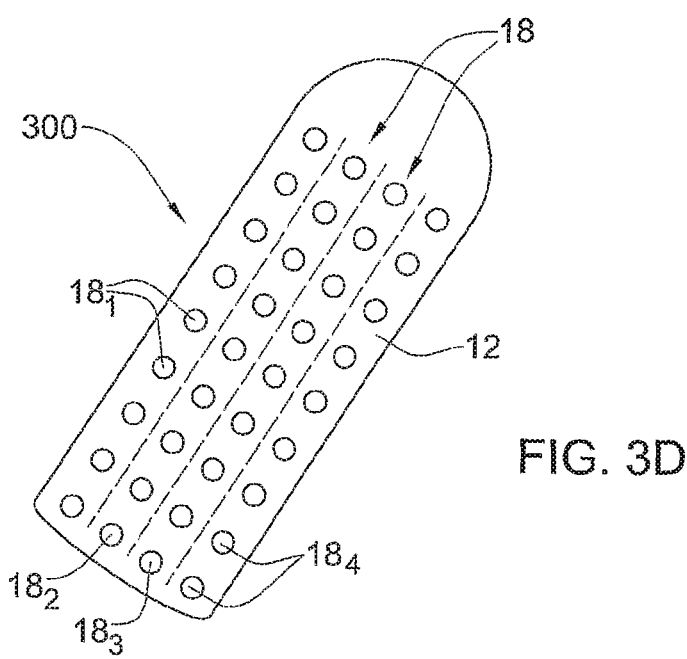
FIG. 3D shows an example of the device of the invention configured to define different groups of light sources producing light components of different wavelengths, respectively.

Reference is made to FIG. 3D illustrating schematically yet another example of the invention. In this example, a probe device 300 includes a probe member 12 configured to define different groups (sub-arrays) of light sources (LEDs) producing light components of different wavelengths, respectively. More specifically, a three-dimensional array of LEDs 18 is arranged in a plurality of sub-arrays, generally $18_i$, four such sub-arrays $18_1$, $18_2$, $18_3$ and $18_4$ being seen in the figure. For example, LEDs $18_1$, $18_2$, $18_3$ and $18_4$ produce light of, respectively, red, blue, green and yellow colors. It should be noted that the probe member may carry a series of such LEDs groups. The sub-arrays $18_i$ are arranged one after the other across the probe member, the LEDs of each sub-array extending also along the probe member. This configuration allows for rotating the probe member while in the body cavity to thereby sequentially subject each region of the inner wall of the body cavity to different wavelengths of illumination. The illumination of different wavelengths may for example be carried out with different illumination conditions, such as pulsed or CW mode, pulse duration and rate, the entire illumination session duration, etc.

It should be understood that the probe configuration of the present invention carrying a three-dimensional array of light sources may also be advantageously used for skin treatment, especially when different illumination conditions are to be successively applied to the skin region. This can be achieved by rotating (with a predetermined rate) the probe member with respect to the body tissue to be treated, thus successively bringing the light source producing light of different color to the treatment region of the body tissue.

Figure 3E:
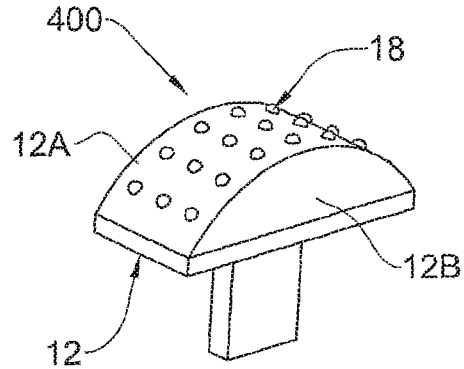
FIGS. 3E and 3F show two more examples, respectively of a probe member configuration suitable to be used in the probe device of the present invention.
Figure 3F:
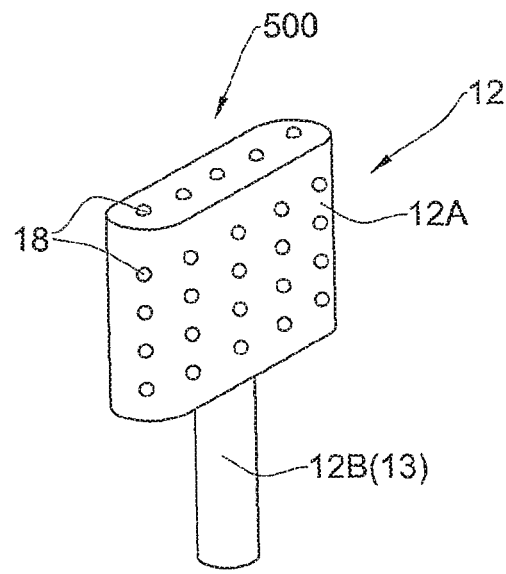

Reference is made to FIGS. 3E and 3F schematically illustrating two more examples of the probe member configuration. In the example of FIG. 3E, a probe device 400 includes a probe member 12 having a curved (parabolic-like) surface 12A carrying a three-dimensional array of light sources 18 (LEDs or optical windows as the case may be), and the opposite substantially planar surface 12B, on which a handle portion 13 is provided. The light sources and control unit may be appropriately configured within and/or outside the probe member as described above. FIG. 3F shows a probe device 500 including a probe member 12 having a first plate-like portion 12A thereof of a substantially rectangular cross-section (e.g. with round edges) carrying light sources 18 arranged in a three-dimensional array within the two opposite surfaces of portion 12A, and a second cylindrically shaped portion 124 that may serve as a handle portion 13.

Figure 3G:
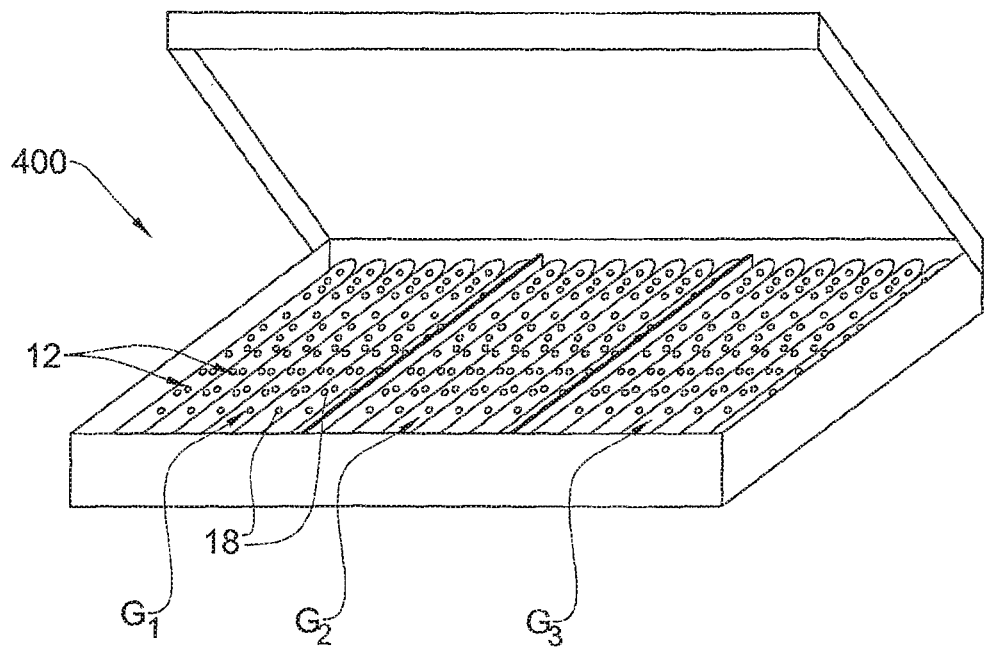
FIG. 3G exemplifies a treatment kit for treatment of a woman's vagina.

Reference is made to FIG. 3G exemplifying some other features of the invention. Considering for example the vagina treatment using a tampon-like probe, the case may be such that a patient is to undergo a 21-day treatment period. In this case it would be convenient to provide the patient with a kit, generally at 400, including a set of for example 21 disposable probe devices or probe members 12 with light sources (light emitters) 18, and written instructions to use the kit (not shown). Moreover, the case may be such that a different combination of colors is to be used at different treatment sessions, thus the light sources combination in different probe members may be different. For example, a group $G_1$ of probes is configured for treatment with a first color or a first combination of colors, and groups $G_2$ and $G_3$ of probes are intended for second and third color (combinations of colors) treatments.

As indicated above, the probe member may be power supplied from a battery or from a power network. Considering the above example of FIG. 3G, it might be preferable to use chemiluminescent light sources rather than those requiring electrical power supply (LEDs).

Figure 4:
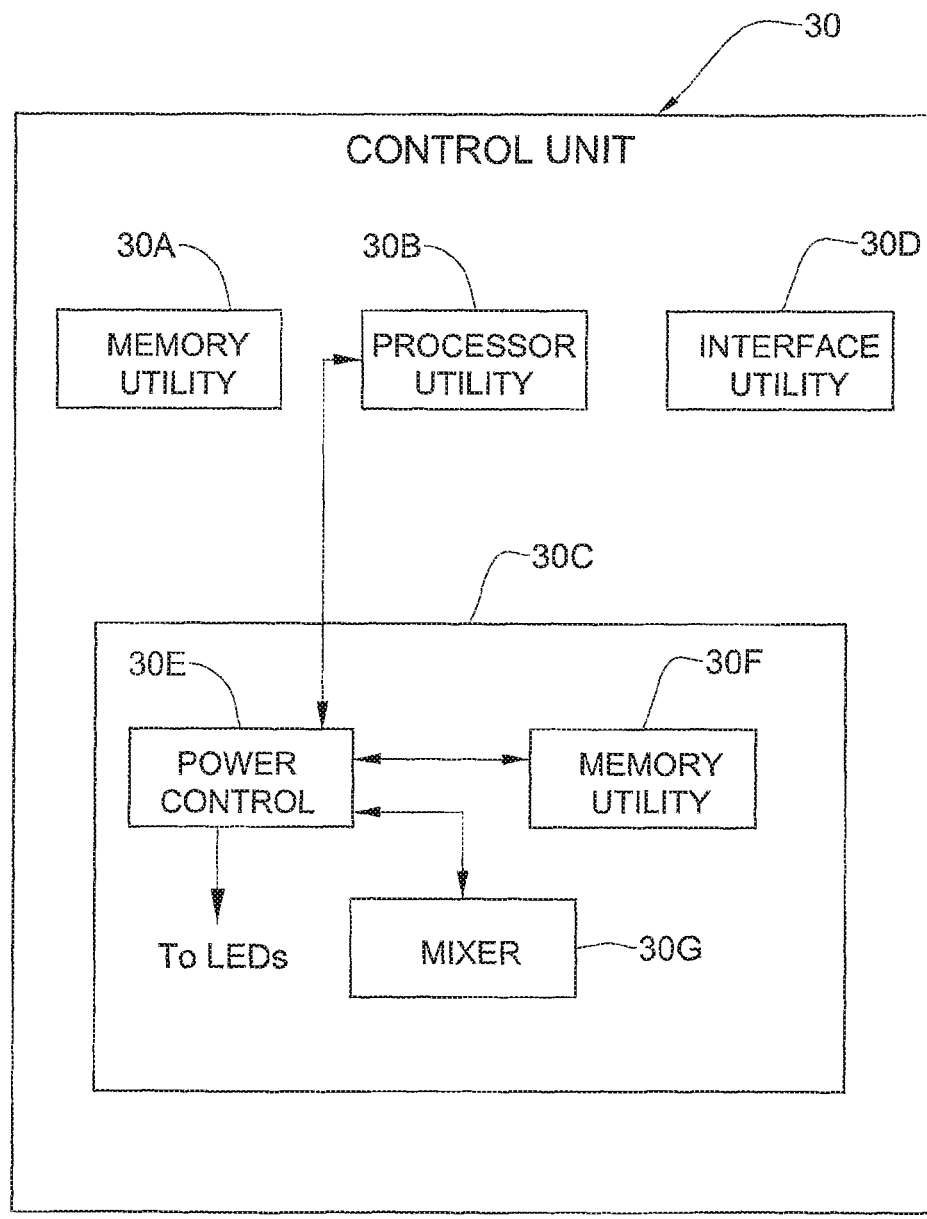
FIG. 4 exemplifies the configuration of a control unit suitable to be used in the present invention for controlling one or more parameters of the illumination.

As indicated above, the invention may utilize a pulse mode of operation of the light emitters, e.g. LEDs. The period of pulsing, as well as the pulse duration and the entire treatment duration is selected in accordance with a specific device application. FIG. 4 exemplifies the configuration of a control unit 30. The latter includes an illumination controller 30C including a power control utility 30E configured and operable by a processor utility (software) 30B for appropriately supplying power to the light emitters (which may be accommodated within the control unit as exemplified in FIG. 3A or may be carried by the probe member as exemplified in FIG. 1A) and varying the intensity of emitted light they produce; a pulse generator unit 30F for setting the frequency and duration of emitted pulses; a mixer 30G for providing an appropriate combination of wavelengths (and/or determining their sequential operation) and power cords and cables to facilitate operation. It should also be noted that the operational mode may be such that the same location on the tissue is sequentially illuminated, by different wavelengths, each being applied with a predetermined operational mode (i.e. pulse or CW and/or duration of the entire illumination and/or intensity and/or pulse duration and period) and/or polarization of light.

Figure 5A:
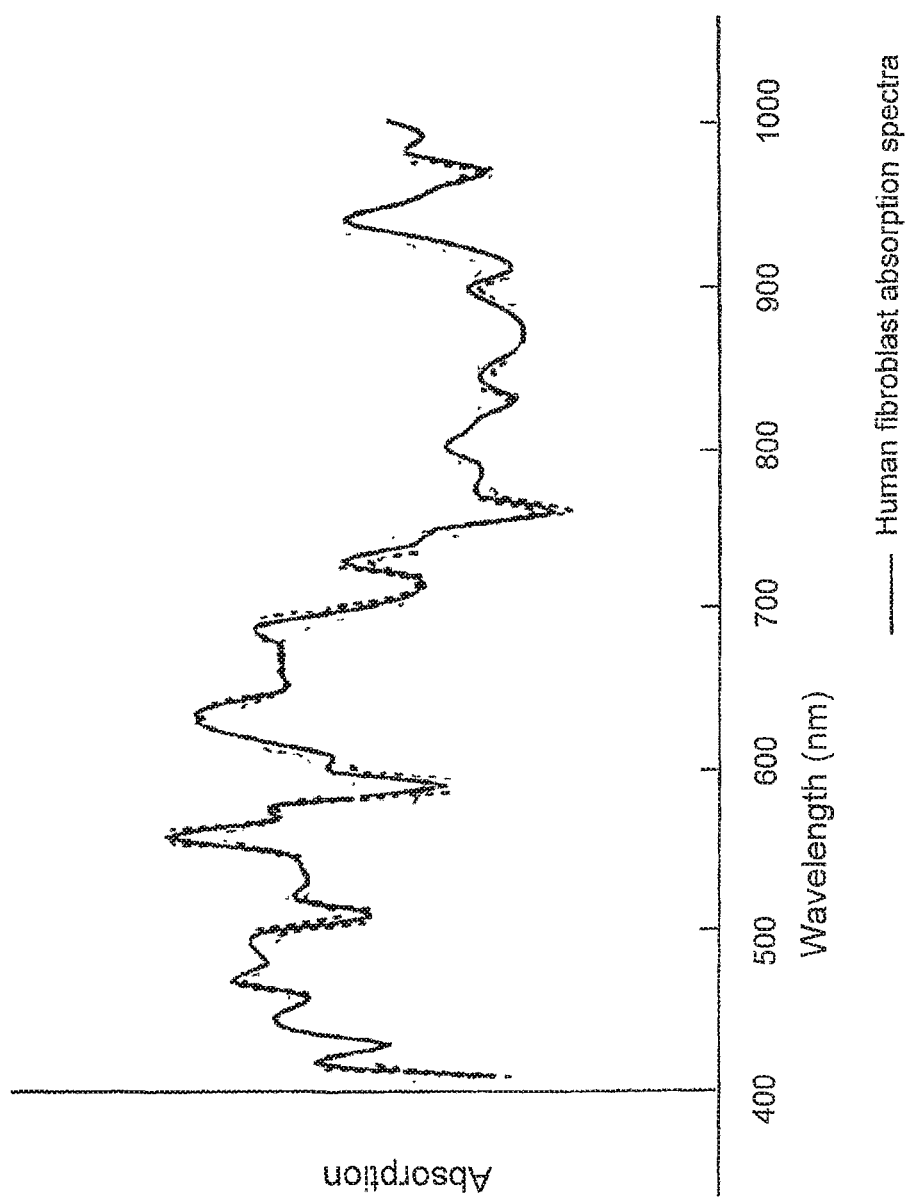
FIGS. 5A-5B show graphs of the absorption spectrum of human fibroblast cells in tissue culture, suitable for determining the operational parameters of the probe device.
Figure 5B:
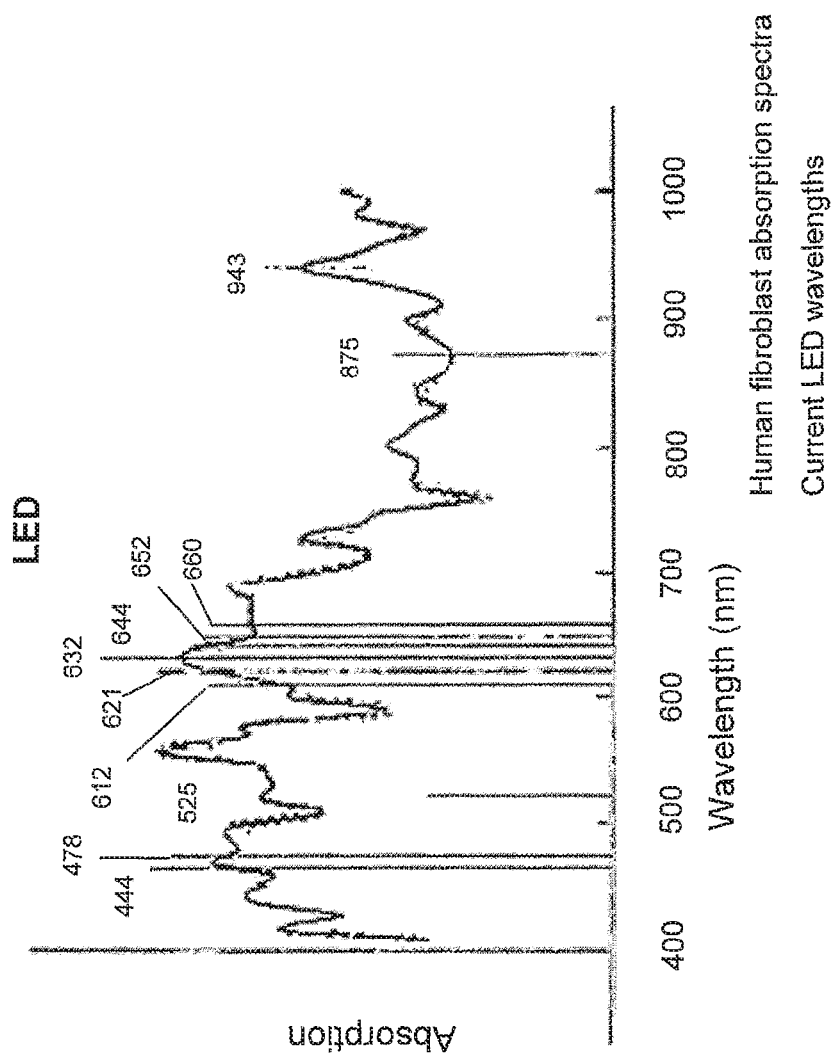

Reference is made to FIGS. 5A-5B showing some examples of how to select the operational parameters of the device for a specific treatment session. FIG. 5A shows the absorption spectrum for human fibroblast cells in tissue culture, which may be used for selection of suitable LED's for use in accordance with the invention. For example, where high absorption by fibroblast cells is desired, a wavelength between about 400 nm and about 700 nm, with fibroblast maximal absorption being in the range of 550-650 nm wavelength, may be selected. FIG. 5B shows the absorption spectra of human fibroblasts in a culture along with the wavelengths of commonly available LED devices, suitable for use in respective applications of the present invention.

DESCRIPTION OF SOME SPECIFIC EXAMPLES

Example 1

Vaginal Rejuvenation

In the following example, subjects are treated in accordance with the invention, for restoring the vaginal wall tightness, tone, elasticity and normal moisture.

Subjects selected for treatment (inclusion criteria) are healthy parous females complaining of one or more of the following symptoms: loosed vagina; sexual dysfunction; excessive odorous discharge; male partner dissatisfaction; embarrassment; emotional distress.

Subjects are treated by exposure of the vagina to light (RGB) according to the following treatment schedule (Table 1):

TABLE 1

Schedule of treatment

| DAY WEEK | 1 | 2 | 3 | 4 | 5 | 6 | 7 |
|---|---|---|---|---|---|---|---|
| 1 | R | R | R | G | Y | Y | R |
| 2 | R | R | R | G | R | R | G |
| 3 | Y | Y | Y | Y | R | Y | Y | where R = Red; G = Green; Y = Yellow.

Recommended treatment continues for a period of three months and includes daily exposure of the vagina to light for 10 minutes. During the period, treatment is ceased (thus, during a month there 21 consecutive days of treatment).

Results are assessed during treatment based on a questionnaire filled by the treated subject comparing the severity of complains before during and after the treatment.

Example 2

Bacterial Vaginosis

Vaginitis (infection of the vagina) is a common gynecologic problem. The most common causes of vaginitis are *Trichomonas vaginalis* infection, vaginal candidiasis, and bacterial vaginosis (By). In the following example subjects are treated in accordance with the invention against bacterial vaginosis in order to restore the normal bacteria flora.

Subjects selected for treatment (inclusion criteria) are females complaining of abnormal or odorous vaginal discharge and pruritus attributed to vaginosis or diagnosed as such by a positive vaginal swab culture.

Subjects are treated for a period of 1 week by exposure of the vagina to light (RGB) according to the following treatment schedule (Table 2):

TABLE 2

Schedule of treatment

| DAY Treatments per day | 1 | 2 | 3 | 4 | 5 | 6 | 7 |
|---|---|---|---|---|---|---|---|
| 1 | B | B | B | B | R | R | B |
| 2 | B | B | R | R | R | B | B |
| 3 | R | R | B | B | R | B | B | where R= Red; B = Blue.

Treatment includes three daily exposures of the vagina, as specified in Table 2, each exposure lasts for 7 minutes, for a total period of 1 week.

Results are exhibited by the restoration of normal vaginal flora and/or relief of symptoms or by obtaining a normal vaginal swab culture.

Example 3

Hemorrhoids

Subjects suffering from internal and/or external hemorrhoids are treated by exposure of the hemorrhoids to light in order to reduce hemorrhoid volume and to prevent hemorrhoid inflammation and pain resulting therefrom.

Subjects selected are those which complain about bleeding, pain or discomfort.

Subjects are treated for a period of 2 weeks by exposure of the hemorrhoids to light (RGB) according to the following treatment schedule (Table 3):

TABLE 3

Schedule of treatment

| DAY → week | 1 | 2 | 3 | 4 | 5 | 6 | 7 |
|---|---|---|---|---|---|---|---|
| 1 | G | G | R | R | G | R | Y |
| 2 | G | R | R | R | G | Y | Y | where R = Red; G = Green; Y = Yellow.

Treatment includes a daily exposure of the homorrhoids, as specified in Table 3, each exposure lasts for 10 minutes, for a total period of 2 weeks or more, according to the condition.

Improvement or efficacy of treatment is exhibited by regression of symptoms associated with hemorrhoid and regression of bleeding.

Example 4

Lacrimal Duct Occlusion

Subjects exhibiting lacrimal duct occlusion (abnormally increased tearing) are selected for this treatment. Treatment is executed by the use of an optical fiber adjacent to the lacrimal duct so as to expose the interior thereof to light (RGB) using red light after covering the eye (in order to prevent exposure of the eye) three treatments per week, lasting 4 minutes each.

Results are determined by reduced tearing and inflammation.

Example 5

Intranasal Treatment

Intranasal administration of drugs has become in the past years a selected route of administration of several drugs, for systemic delivery. Blood levels of the administered drug may be elevated by pre-treating the intranasal cavity by increase in drug absorption at that site. Drug absorption may be increase by radiation of the inner walls of the nostrils by light. The following example makes use of red light, although other wavelengths and optical energy may be applicable as well. Subjects selected for treatment are those in which there is interest in reducing nasal mucosa congestion, (hey fever, allergy) or suffering of intranasal polyps, or prior to a scheduled nasal administration of drugs (such as special fertility drugs).

Subjects are treated by exposure of the intranasal cavity to red light for 5 minutes prior to or 3 minutes prior and 3 min immediately after administration of the drug to the treated cavity.

Treatment efficacy is exhibited by increased blood levels of the drug and improved drug efficacy as compared to treatment without radiation (control group).

The invention claimed is:

1. A probe device for use in treatment of tissues lining a body cavity having an orifice on an external surface of the body and an inner wall covered by biological vital cell containing tissue, the probe device comprising:
   a probe member comprising a tampon shaped portion, said tampon shaped portion comprising a distal end having a generally hemispherical surface with no outwardly facing protrusions, a proximal end, and a cylindrical portion connecting the proximal end to the distal end, said tampon shaped portion having dimensions and shape suitable for insertion into said body cavity via the orifice and defining an illumination surface for facing an inner wall of the body cavity,
   one or more light guides disposed in the cylindrical portion,
   a plurality of optical windows arranged in a spaced-apart relationship around an entire circumference of the surface of only said cylindrical portion with either random distribution or a specific distribution pattern along said surface, said optical windows being optically coupled to said one or more light guides and comprising at least one of lenses, polarizers, and/or translucent light diffusers to provide substantially uniform illumination of the inner wall of the body cavity by said illumination surface, said illumination surface comprising said entire circumference of the tampon shaped portion with said optical windows to allow optical energy, passing through said optical windows, to be directed outwardly from said illumination surface and provide substantially uniform illumination of an entire treatment region within the inner wall of the body cavity,
   one or more light emitters located outside said cylindrical portion of the probe member, and optically coupled to said one or more light guides extending inside the cylindrical portion between said one or more light emitters and said optical windows on the surface of the cylindrical portion, such that said one or more emitters are optically coupled to the optical windows via said one or more light guides, said one or more light emitters being configured and operable to emit light of one or more selected wavelengths within the visible spectral range, and
   an illumination controller connected to said one or more light emitters configured to control emission of the one or more selected wavelengths, to thereby controllably illuminate the inner wall of the body cavity, via said optical windows, with the one or more selected wavelengths selected to affect one or more of the following: tissue rejuvenation, blood circulation, pathogen infection treatment, to thereby increase flexibility, elasticity and firmness of the body cavity inner wall.

2. The probe device of claim 1, wherein said one or more light emitters comprise one or more light emitting diodes (LEDs).

3. The probe device of claim 1, wherein said light sources are arranged in a three-dimension array within said at least portion of the probe member, to thereby direct the light components outwardly from said at least portion of the probe member in different directions.

4. The probe device of claim 1, wherein said one or more light guides comprise one or more optical fibers.

5. The probe device of claim 4, wherein each of the optical windows is optically coupled to a dedicated segment of the one or more optical fibers.

6. The probe device of claim 1, comprising a biocompatible cover above said arrangement of the light sources on at least said tampon portion of the probe member.

7. The probe device of claim 6, wherein said cover is removably mountable onto at least said tampon portion of the probe member.

8. The probe device of claim 1, wherein said illumination controller is further configured and operable for adjusting one or more of the following operational parameters of said one or more light emitters: an operational mode of the light emitter to emit the light in series of pulses and/or continuous-wave mode of illumination, a duration of each light pulse, an interval between adjacent pulses of light, a period and number of pulses of light, an intensity of the light, polarization of light, and a duration of the emission process.

9. The probe device of claim 8, wherein said illumination controller comprises a mixer utility for mixing light of different wavelengths emitted by the light emitters to obtain a desired wavelength at the output of each of the optical windows.

10. The probe device of claim 8, wherein said illumination controller is configured and operable to provide a predetermined sequence of wavelengths to at least one of the light sources to thereby enable sequential illumination with different wavelengths at least a specific location on cavity wall tissue.

11. The probe device of claim 1, said one or more selected wavelengths include wavelengths in a range from 380 nm to 740 nm.

12. The probe device of claim 1, wherein said one or more light emitters are configured and operable to emit light of different wavelengths including wavelengths in a range from 380 nm to 740 nm.

13. The probe device of claim 1, wherein said one or more light emitters are configured and operable to emit light of different wavelengths, said different wavelengths including wavelengths of yellow color and at least one of red, green or blue colors.

14. The probe device of claim 1, wherein said illumination controller is configured and operable in accordance with predetermined reference data defining operational mode of said one or more light emitters in accordance with a user's treatment program.

15. A method for photobiomodulation of a body cavity having a wall, such as vagina, rectum, nostrils, oral cavity, uterus, the method comprising illuminating at least part of said wall with light of different wavelengths using the probe device of claim 4, said illuminating comprising controlling one or more of the following operational parameters: an operational mode of each of the light sources to direct the light component in serious of pulses and/or continuous-wave mode of illumination, a duration of each light pulse, an interval between adjacent pulses of light, a period and number of pulses of light, an intensity of the illuminating light, wavelengths of the illuminating light, polarization of light, a duration of the illumination process; and providing a predetermined sequence of wavelengths to at least one of the light source to thereby enable sequential illumination with different wavelengths at least a specific location on cavity wall tissue.

16. The method of claim 15, wherein said different wavelengths include wavelengths in a range from about 300 nm to about 1200 nm.

17. The method of claim 15, wherein said different wavelengths include wavelengths in a range from about 300 nm to about 800 nm.

18. The method of claim 15, wherein said different wavelengths include wavelengths of yellow color and at least one of red, green or blue colors, thereby providing an effect on tissue rejuvenation in combination with at least one of the following: affecting blood circulation in the cavity wall tissue, and affecting bacteria for pathogen infection treatment.

19. The method of claim 15, wherein said illuminating provides modulation of one or more of the following parameters:
  increase in mucous secretion at said body cavity;
  increase in elasticity of the wall of said body cavity;
  increase in firmness of the wall of said body cavity;
  increase of blood circulation in blood vessels adjacent to the wall of said body cavity;
  increase tissue vitality;
  decrease in diameter of said body cavity.

* * * * *